US008753279B2

(12) United States Patent
Tanaka et al.

(10) Patent No.: US 8,753,279 B2
(45) Date of Patent: Jun. 17, 2014

(54) ULTRASOUND PROBE AND ULTRASOUND IMAGING DEVICE

(75) Inventors: Hiroki Tanaka, Musashino (JP); Shuntaro Machida, Kokubunji (JP)

(73) Assignee: Hitachi Medical Corporation, Tokyo (JP)

( * ) Notice: Subject to any disclaimer, the term of this patent is extended or adjusted under 35 U.S.C. 154(b) by 29 days.

(21) Appl. No.: 13/386,120

(22) PCT Filed: Aug. 11, 2010

(86) PCT No.: PCT/JP2010/063607

§ 371 (c)(1), (2), (4) Date: Jan. 20, 2012

(87) PCT Pub. No.: WO2011/033887

PCT Pub. Date: Mar. 24, 2011

(65) Prior Publication Data

US 2012/0123268 A1 May 17, 2012

(30) Foreign Application Priority Data

Sep. 17, 2009 (JP) ................................ 2009-215755

(51) Int. Cl.
*A61B 8/00* (2006.01)
*A61B 8/14* (2006.01)

(52) U.S. Cl.
USPC ............................ 600/443; 600/437; 600/459

(58) Field of Classification Search
USPC .......................................... 600/443, 459, 437
See application file for complete search history.

(56) References Cited

U.S. PATENT DOCUMENTS 5,902,242 A * 5/1999 Ustuner et al. ................ 600/443
6,359,367 B1 3/2002 Sumanaweera et al.
7,410,950 B2 * 8/2008 Garry et al. .................... 514/1.1
7,449,821 B2 * 11/2008 Dausch ......................... 310/364
2004/0190377 A1 * 9/2004 Lewandowski et al. ...... 367/174
2004/0266362 A1 * 12/2004 Watkins et al. ................. 455/78
2005/0177045 A1 8/2005 Degertekin et al.
2006/0004289 A1 * 1/2006 Tian et al. ..................... 600/459
2007/0267945 A1 * 11/2007 Sudol ............................ 310/334
2009/0301200 A1 12/2009 Tanaka et al.
2010/0156244 A1 * 6/2010 Lukacs et al. ................. 310/335

FOREIGN PATENT DOCUMENTS

CN 101006361 A 7/2007
CN 101238754 A 8/2008
JP 2007-318742 12/2007
JP 2008-510324 4/2008
WO 2007/046180 4/2007

OTHER PUBLICATIONS

Robert D. Blevins, "Formulas for Natural Frequency and Mode Shape", ISBN 1-57524-184-6.
International Search Report and Written Opinion for PCT International Application No. PCT/2010/063607, mailed on Dec. 7, 2010.
Robert D. Blevins, "Formulas for Natural Frequency and Mode Shape", ISBN 1-57524-184-6, 1979.

* cited by examiner

*Primary Examiner* — Tse Chen
*Assistant Examiner* — Lisa Kinnard
(74) *Attorney, Agent, or Firm* — Brundidge & Stanger, P.C.

(57) ABSTRACT

Spurious response resulting from a high-order vibration mode that occurs when the cell shape of a capacitive micro-machined ultrasonic transducer is anisotropic is reduced. Assuming that a ratio between a long direction (l) and a short direction (w) of a diaphragm forming a capacitive micro-machined ultrasonic transducer is a representative aspect ratio (l/w), the representative aspect ratio is set to a value at which a dip of 6 dB or greater would not be formed within a transmit and receive bandwidth of a probe. Alternatively, the representative aspect ratio is so set that there would be six or more vibration modes for which the value obtained by dividing the frequency of a vibration mode having an odd number of anti-nodes by a fundamental mode frequency would be 2 or less.

11 Claims, 13 Drawing Sheets

ULTRASOUND PROBE AND ULTRASOUND IMAGING DEVICE

TECHNICAL FIELD

The present invention relates to an ultrasonic probe and ultrasonic imaging device, and, by way of example, to an ultrasonic probe and ultrasonic imaging device that use capacitive micro-machines.

BACKGROUND ART

Ultrasonic transducers are devices that radiate and receive sound waves in or above the audible range (approximately 20 Hz to 20 kHz), and are widely used for medical purposes, in non-destructive testing, etc. Piezoelectric devices, a typical example being PZT (Lead Zirconate Titanate), are presently most widely used as ultrasonic transducers. However, in recent years, the development of ultrasonic devices called Capacitive Micro-machined Ultrasonic Transducers (hereinafter, CMUTs), which utilize an operation principle that differs from piezoelectric types, has advanced, and is beginning to be put to practical use. CMUTs are fabricated by applying semiconductor techniques. They are ordinarily formed by burying an electrode material in a substrate (or the substrate itself may sometimes serve as an electrode) made of a material that is used in semiconductor processes, e.g., silicon, etc., and by securing a fine (e.g., 50 μm) and thin (e.g., several μm) diaphragm with supporting walls around the diaphragm, etc. A cavity is provided between the diaphragm and the substrate to allow the diaphragm to vibrate. An electrode material is buried within this diaphragm as well. By thus having independent electrodes disposed in the substrate and the diaphragm, the substrate and the diaphragm function as a capacitance (capacitor). By applying a voltage across both electrodes (a bias voltage is ordinarily applied in advance), they function as an ultrasonic transducer. When an AC voltage is applied across both electrodes, the electrostatic force between the electrodes varies, causing the diaphragm to vibrate. If, at this point, there is some medium that is in contact with the diaphragm, the vibration of the diaphragm will propagate within the medium as a sound wave. In other words, it is possible to radiate sound. Conversely, if a sound wave is transmitted to the diaphragm, the diaphragm will vibrate in accordance therewith, and as the distance between both electrodes varies, an electric current will flow between both electrodes, or the voltage across both electrodes will vary. By extracting an electric signal of this electric current, voltage, etc., it is possible to receive sound waves.

Important indicators that determine the performance of an ultrasonic transducer include the acoustic pressure transmitted and receive sensitivity. To increase acoustic pressure and receive sensitivity, the greater the area that vibrates, the better. The area that vibrates is dependent on the shape of the diaphragm. In the case of a circular, square or regular hexagonal diaphragm, since the diaphragm is secured from around in a generally uniform manner, the diaphragm is only able to vibrate near its center. As a result, in effect, only approximately 30 to 40% of the cavity area is used effectively. On the other hand, in the case of an elongate rectangular (oblong) diaphragm, the extent to which it is bound from around is mitigated, and displacement in a more even manner becomes possible as compared to a circular diaphragm, etc. In this case, approximately 60% of the area vibrates effectively. Thus, from the standpoint of improving acoustic pressure and receive sensitivity, an elongate rectangular shape is preferable. However, when a shape that is elongate to some extent is adopted, as in a rectangular diaphragm, characteristic high-order vibration modes occur. The various vibration modes that occur in the diaphragm have an influence on acoustic characteristics, e.g., radiated acoustic pressure, frequency characteristics, pulse characteristics. Accordingly, controlling vibration modes becomes extremely important.

PRIOR ART DOCUMENTS

Patent Documents

Patent Document 1: U.S. Pat. No. 6,359,367
Non-Patent Documents
Non-Patent Document 1: Formulas for Natural Frequency and Mode Shape, Robert D. Blevins, ISBN 1-57524-184-6

SUMMARY OF THE INVENTION

Problems to be Solved by the Invention

Various vibration modes may be excited in the diaphragm of a CMUT. Ordinarily, when using an ultrasonic transducer, of the innumerable vibration modes that exist, a mode called fundamental mode where the diaphragm as a whole vibrates in phase is preferable. The reason being that because the diaphragm as a whole moves in phase, it is possible to convert sound and electricity most efficiently. In the case of a mode called high-order mode where a plurality of parts that serve as anti-nodes are created in the diaphragm, there will be places within the diaphragm where the vibration phases differ by 180 degrees. When sound is radiated in such a mode, a given region of the diaphragm may vibrate in a direction that compresses the medium that is in contact with the diaphragm, thereby radiating a positive pressure (compression wave), while simultaneously at another region of the diaphragm, the medium may be expanded, thereby radiating a negative pressure (expansion wave). Thus, the positive and negative sounds would cancel each other out, causing the net radiated acoustic pressure to drop. Similarly, in the case of reception, if there is a region where the diaphragm's displacement is in the opposite direction relative to the inputted acoustic pressure, sensitivity would drop since the positive and negative receive currents or voltages would cancel each other out.

Such phenomena are not problems of individual vibration modes, but instead have influences in the form of interference among separate vibration modes as well. In general, when some medium that radiates energy is in contact with the diaphragm, the individual vibration modes each possess a bandwidth to some degree. Thus, there exists a region where the band of the fundamental mode overlaps with the band of a high-order mode. In this case, there arises a frequency where the phase of the fundamental mode does not match with the phase of the high-order mode, and by a similar mechanism as that discussed above, there occurs a drop in radiated acoustic pressure or sensitivity. Accordingly, in order to widen the available frequency band, interference among the vibration modes must be considered.

On the other hand, the vibration modes of a diaphragm are dependent on the diaphragm's shape and boundary conditions. In the case of a shape where the distance from the center of the diaphragm to the supporting walls that bind the diaphragm may be considered uniform, e.g., a circular shape, or a regular polygonal shape such as a regular hexagonal shape, which are widely in use, the resonance frequencies of the fundamental mode and a high-order mode would always be of a constant ratio. Accordingly, once the shape is determined, the frequency characteristics are uniquely determined. On the other hand, if the distance from the center of the diaphragm to the surrounding supporting walls is not uniform and there is anisotropy, by way of example, in a case where the diaphragm shape is an elongate rectangular shape, the frequency of the excited vibration mode would vary largely depending on the ratio of the length of the longer side of that diaphragm to the width of the shorter side (i.e., the aspect ratio between representative long and short lengths (representative aspect ratio), or in the case of a rectangle, the length-to-width aspect ratio). Accordingly, in order to secure some available bandwidth, it is necessary that the aspect ratio of the representative lengths of the diaphragm be set appropriately.

An object of the present invention is to reduce the influences of the individual vibration modes and of interference among the vibrations on acoustic characteristics even in cases where the shape of the diaphragm of a capacitive micro-machine is such that the distance from the diaphragm center to the supporting posts that bind the diaphragm is not isotropic.

Means for Solving the Problems

In cases where the diaphragm has a shape that is elongate to some extent, a typical example being a rectangular diaphragm, the vibration modes that are excited in the longer direction and shorter direction of the diaphragm may be considered separately. Of the vibration modes that are determined by the width of the diaphragm in the direction of the short side, the one with the lowest frequency becomes the resonance frequency of the fundamental mode. On the other hand, although the vibration mode frequencies in the lengthwise direction of the diaphragm are ordinarily higher than the resonance frequency of the fundamental mode, as its length becomes longer relative to the width in the short direction (i.e., as the long to short aspect ratio becomes greater), the resonance frequencies of the high-order modes approach the resonance frequency of the fundamental mode. In the case of a finite aspect ratio, there exist points within the band of the fundamental mode where a drastic drop in sensitivity occurs due to interference with high-order modes. On the other hand, in the case of an aspect ratio that is infinitely long, the resonance frequencies of all the high-order modes that are excited in the lengthwise direction of the diaphragm converge towards the fundamental mode frequency. In this case, since the inter-mode interferences all cancel one another out, it becomes equivalent to a state where only the fundamental mode is vibrating. With an actual diaphragm, it is not possible to create an infinite aspect ratio. However, it is possible to create a state that may be deemed the same as an infinite aspect ratio for practical purposes by making the aspect ratio be greater than a certain value. In so doing, since local sensitivity reduced regions that occur due to inter-mode interference may be suppressed, it is possible to attain characteristics that are more wide band in practical terms.

As such, in a case where the distance from the center of the diaphragm to the supporting walls is not uniform, the present invention sets the ratio of the length of the diaphragm in the direction of a first axis to the length in the direction of a second axis that is perpendicular to the first axis (i.e., representative aspect ratio) to a value that allows a signal level of a locally occurring frequency at which the amplitude drops or the sensitivity drops to be suppressed below a predetermined value within a bandwidth of at least one of transmission and reception by an ultrasonic probe.

An ultrasonic probe of the present invention comprises a capacitive micro-machine and at least one or more acoustic media that are in contact with the capacitive micro-machine. The capacitive micro-machine comprises a substrate having a first electrode and a diaphragm having a second electrode, wherein the diaphragm is secured to the substrate at its peripheral parts by means of supporting walls that rise from the substrate, and a cavity is formed between the substrate and the diaphragm. The ultrasonic probe is characterized in that the ratio of, of the representative dimensions of the diaphragm of the ultrasonic probe, the short direction to the long direction is equal to or greater than a value that does not cause acoustic performance degradation within a used sensitivity band.

Effects of the Invention

The present invention realizes an ultrasonic probe that suppresses spurious response caused by high-order vibration modes and that may be used in a wider band.

MODES FOR CARRYING OUT THE INVENTION

Embodiments of the present invention are described below. It is noted that the contents of the cell structures and device configurations discussed herein are merely examples, and that other embodiments may be realized through combinations and replacements of the embodiments with known techniques.

[First Embodiment]

Figure 1:
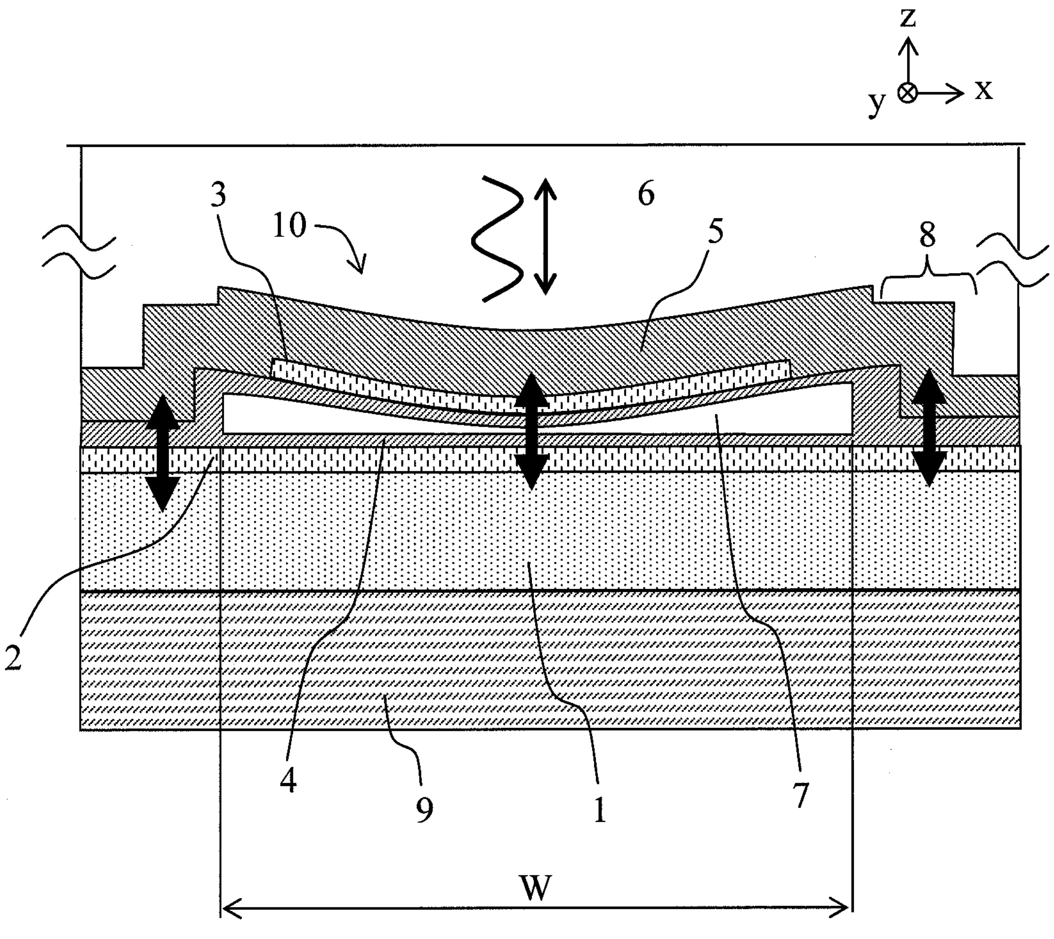
FIG. 1 is a schematic sectional view of a capacitive micro-machined ultrasonic transducer.
Figure 2:
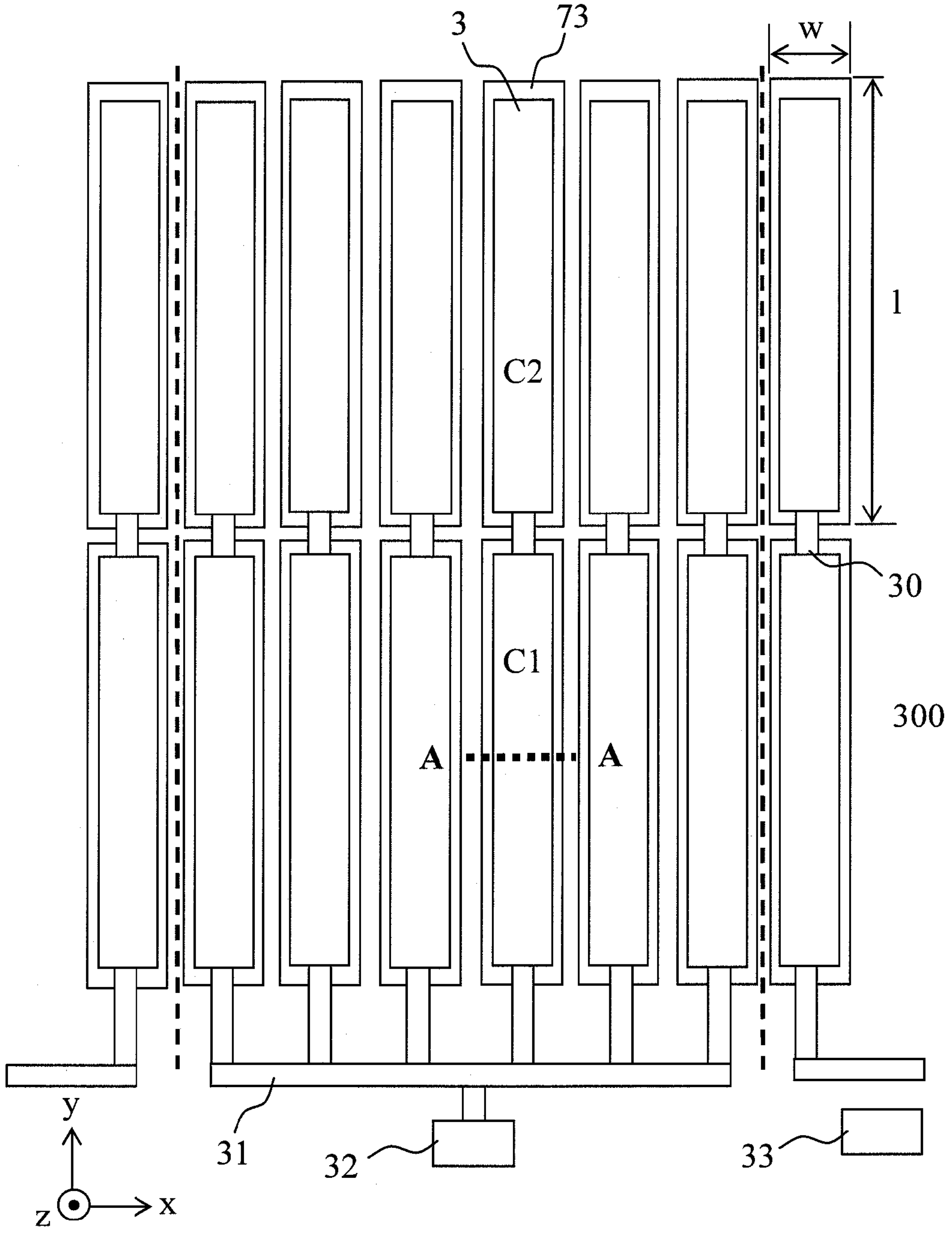
FIG. 2 is a schematic plan view of a capacitive micro-machined ultrasonic transducer array (rectangle).

FIG. 1 is a vertical sectional view of a CMUT (10) of the first embodiment. FIG. 2 is a plan view thereof. The crosssection taken along AA in FIG. 2 corresponds to FIG. 1. For purposes of convenience, the direction in which the CMUT (10) transmits ultrasound, that is, the upward direction in FIG. 1 and the perpendicularly upward direction relative to the plane of the sheet of FIG. 2, is taken to be the z-direction. Further, the rightward direction in FIG. 1 and FIG. 2 is taken to be the x-direction, and the perpendicularly downward direction relative to the plane of the sheet of FIG. 1 and the upward direction in FIG. 2 are taken to be the y-direction.

As shown in FIG. 1 and FIG. 2, this CMUT (10) is such that a thin film lower electrode 2 comprising a conductor such as aluminum, tungsten, etc., is formed on a flat substrate 1 comprising an insulator or semiconductor, such as silicon single crystal, etc., and a diaphragm 5 is formed above the lower electrode 2. The silicon substrate may sometimes double as the lower electrode. The diaphragm 5 has its peripheral parts secured to the substrate by means of supporting walls 8 that rise from the substrate. A cavity 7 whose perimeter is sealed by the supporting walls 8 is formed between the diaphragm 5 and the substrate 1. An upper electrode 3 that is covered by an insulator 4 is disposed in the diaphragm 5. When a voltage is applied across the lower electrode 2 and the upper electrode 3, the upper electrode 3 is displaced towards the substrate due to electrostatic force. In order to prevent this displacement from becoming so excessive as to place the upper electrode 3 in contact with the lower electrode 2 thereby allowing conduction, it is preferable that the upper part of the lower electrode 2 or the upper electrode 3 be covered with the insulator 4. When the CMUT is actually used, the surface of the diaphragm 5 is ordinarily placed in contact with some acoustic medium 6 that propagates ultrasonic waves, e.g., air, water, etc. Further, a backing material 9 for attenuating sound may sometimes be adhered below the substrate 1.

Assuming that the CMUT (10) shown in FIG. 1 is one element, FIG. 2 shows a CMUT array 300 in which innumerable similar elements are arranged in an array. Thus, instead of being used as a single element, CMUTs may be used by arranging a plurality of elements. In addition, the upper electrodes (C1, C2 in FIG. 2) of a plurality of elements may be electrically interconnected with connector parts 30 and be used as one channel as well. Ordinarily, the connecting of the upper electrodes 3 to an electric circuit is carried out by means of an upper electrode connection pad 32 via lead wires 31. Similarly, the lower electrodes are also made connectable to an electric circuit by means of a lower electrode connection pad 33.

It is noted that the diaphragm 5 and the upper electrode 3 of the present embodiment are depicted as rectangles of the same size. However, with respect to the present invention, the shapes and sizes need not necessarily be rectangular as in FIG. 2, and may instead be some other polygon as in FIG. 3, for example. Further, the sizes of the diaphragms 5 and upper electrodes 3 forming the CMUT array 300 also need not be all uniform. In other words, diaphragms 5 and upper electrodes 3 of varying sizes may be mixed within the CMUT array 300.

The substrate 1, the lower electrode 2, the diaphragm 5, the supporting walls 8, the insulator 4, and the upper electrode 3 are made of materials that may be processed by semiconductor process techniques. By way of example, the materials disclosed in U.S. Pat. No. 6,359,367 may be used. To provide examples, they may include silicon, sapphire, glass materials of all types, polymers (such as polyimide), polysilicon, silicon nitride, silicon oxynitride, thin film metals (such as aluminum alloys, copper alloys and tungsten), spin-on-glasses (SOGs), implantable or diffused dopants and grown films such as silicon oxides and nitrides. The interior of the cavity 7 may be a vacuum, or be filled with air or some gas. When stationary (i.e., when not operating), the gap of the cavity 7 (in the z-direction) is maintained mainly by virtue of the rigidity of the substrate 1, diaphragm 5, supporting walls 8 and upper electrode 3.

Figure 4:
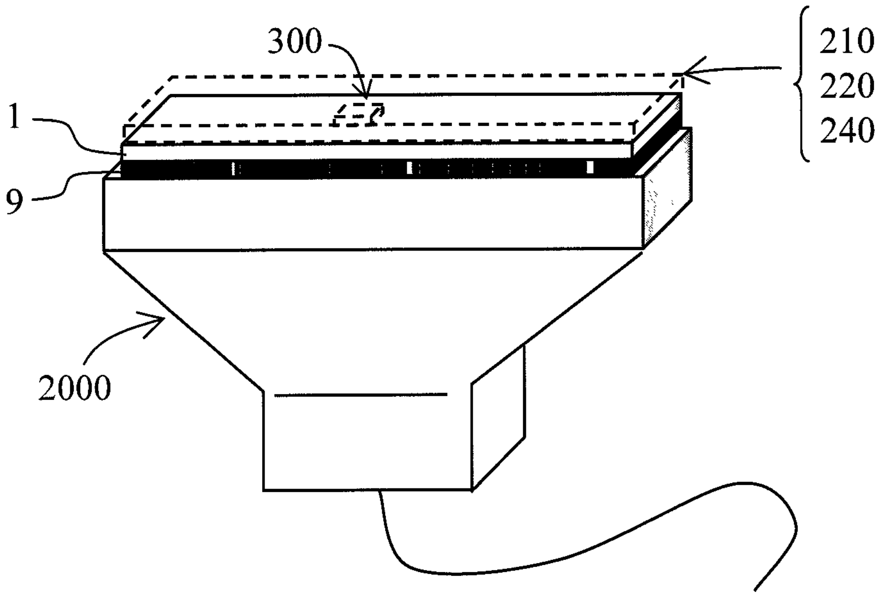
FIG. 4 is an external view of an ultrasonic probe that uses a capacitive micro-machined ultrasonic transducer.

FIG. 4 is an external view where the CMUT array 300 is assembled as an ultrasonic probe 2000. On the medium (subject) side of the CMUT array 300 are disposed an acoustic lens 210 that focuses the ultrasonic beam, an acoustic matching layer 220 that matches the acoustic impedances of the CMUT and the medium (subject), and a conductive film 240 as an electrical shield layer. Further, it may be used with the backing material 9, which absorbs the propagation of ultrasound waves, provided on the back side (the opposite side relative to the medium side).

Figure 3:
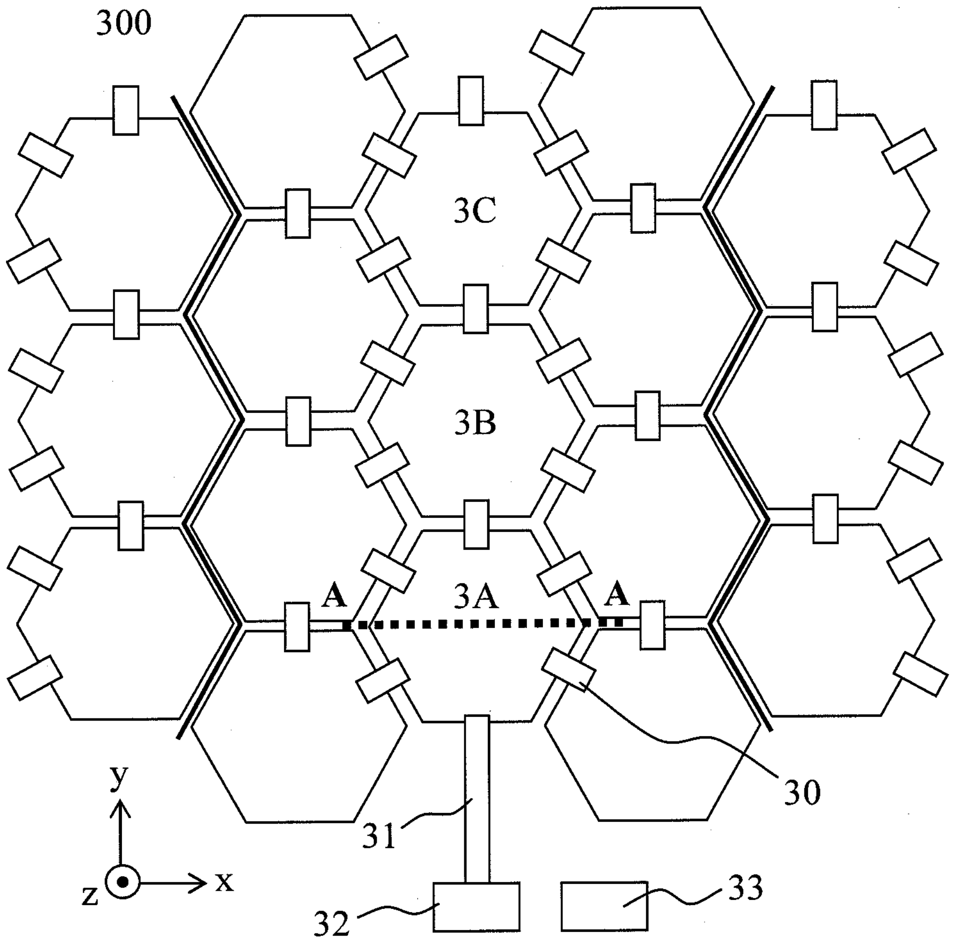
FIG. 3 is a schematic plan view of a capacitive micro-machined ultrasonic transducer array (regular hexagon).
Figure 5:
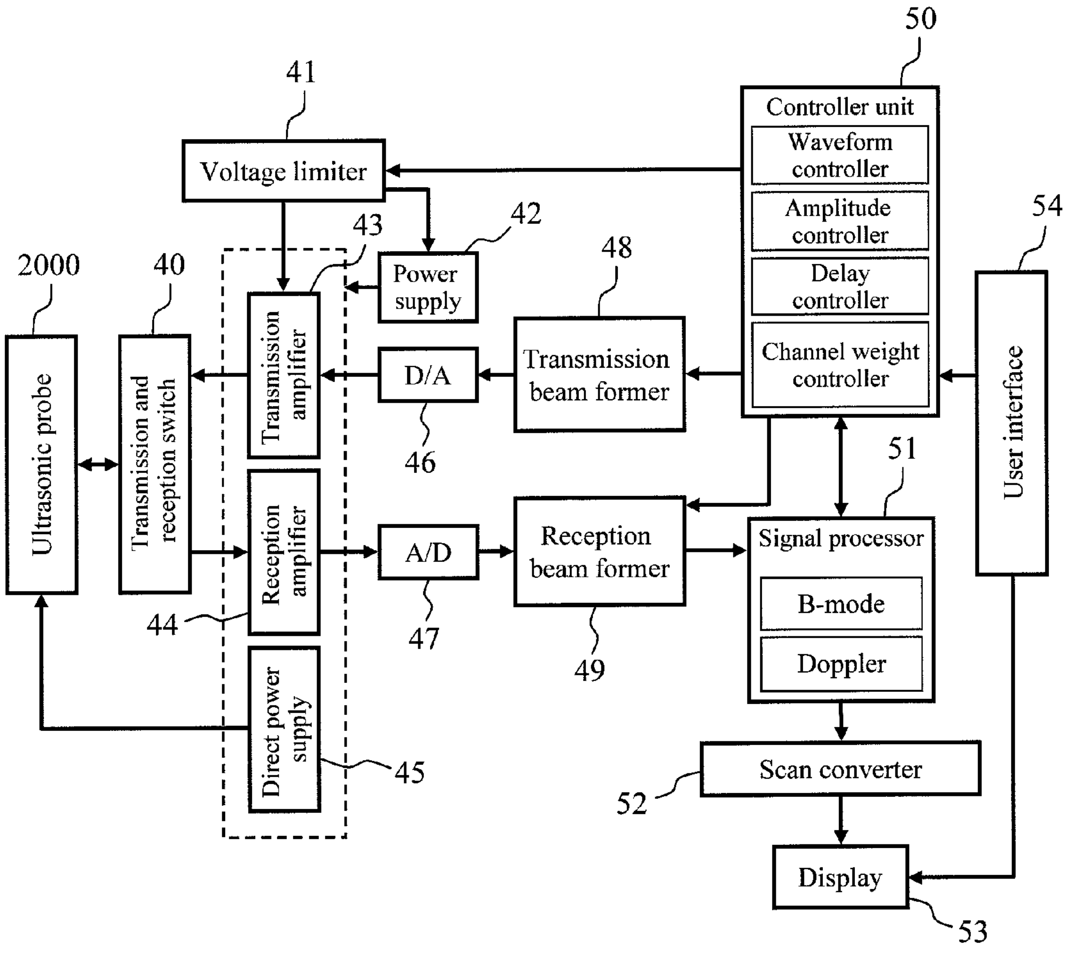
FIG. 5 is a diagram showing a system configuration example of an ultrasonic imaging device.

FIG. 5 is a diagram showing a device configuration example of an ultrasonic imaging device. As shown in FIGS. 1 to 3, each CMUT element, or a group of CMUT elements comprising a predetermined number thereof, is connected to a transmission beam former 48 and reception beam former 49 of an ultrasonic imaging device comprising such an ultrasonic probe 2000 via a transmission and reception switch 40. The ultrasonic probe 2000 operates as an array that forms an ultrasonic beam by means of a direct power supply 45, transmission amplifier 43, and reception amplifier 44 that are driven by a power supply 42, and is used to transmit and receive ultrasonic waves. The transmit and receive signals are controlled by a controller unit 50 in accordance with the purpose. By way of example, with respect to signals, the controller unit 50 executes waveform control, amplitude control, delay control, channel weighting control, etc. The transmit signal is controlled at the controller unit 50, and a voltage is applied to the electrode of each cell or of a channel of a group of cells with the desired waveform, amplitude and delay time set via the transmission beam former 48, a D/A converter 46, and the transmission amplifier 43. Further, a voltage limiter 41 is provided to prevent an excessive voltage from being applied to the probe or for the purpose of transmit waveform control. After going through the reception amplifier 44, an A/D converter 47, and the reception beam former 49, the receive signal is converted to a video signal at a signal processor 51 through B-mode sectional image processing or Doppler processing, and displayed on a display 53 via a scan converter 52.

It is noted that the arrangement of the CMUT array 300 shown in FIG. 2 is only an example, and that other arrangement configurations such as concentric circles, grid-like, irregular intervals, etc., are also possible. Further, the arrangement plane may be flat as well as curved, and the shape of that plane may be circular, polygonal, etc. Alternatively, the CMUTs (10) may be arranged linearly or along a curve. In addition, a portion of the functions shown in FIG. 5 may be incorporated into the ultrasonic probe 2000. By way of example, even if electric circuits such as the transmission and reception switch, reception amplifier, etc., were incorporated into the ultrasonic probe 2000, it would make no difference functionally.

Next, the operation principles of a CMUT are described. The CMUT (10) functions as a variable capacitor in which the lower electrode 2 and the upper electrode 3 are disposed with the cavity 7 and insulator 4 in-between. When a force is exerted on the upper electrode 3 to displace it in the z-direction, the gap between the lower electrode 2 and the movable upper electrode 3 varies, causing the capacitance of the CMUT to vary. Since the upper electrode 3 and the diaphragm 5 are coupled, the upper electrode 3 is also displaced when a force is exerted on the diaphragm 5. In this case, when a voltage is applied across the lower electrode 2 and the upper electrode 3 and a charge is accumulated, the temporal change in the gap between the lower electrode 2 and the upper electrode 3 becomes a temporal change in capacitance, and a new voltage is generated across both electrodes. Thus, when a force that causes some mechanical displacement, such as an ultrasonic wave, etc., is transmitted to the diaphragm 5, that displacement is converted into an electrical signal (voltage or current). In addition, when a difference in potential is imparted between the lower electrode 2 and the upper electrode 3, charges of respectively different signs are accumulated in the electrodes, an attracting force is generated between the electrodes due to an electrostatic force, and the upper electrode 3 is displaced towards the substrate 1. In this case, since the upper electrode 3 and the diaphragm 5 are coupled, the diaphragm 5 is also simultaneously displaced. Thus, if an acoustically propagating medium, such as air, water, plastic, rubber, a living organism, etc., exists above (i.e., in the z-direction of) the diaphragm, the displacement of the diaphragm 5 is transmitted to the medium. The displacement may also be temporally varied by temporally varying the voltage applied across the electrodes, as a result of which sound is radiated. In other words, this CMUT (10) functions as an electroacoustic transducer having the function of radiating an inputted electrical signal to a medium that is in contact with the diaphragm 5 as an ultrasonic signal, and of conversely converting an ultrasonic signal from the medium into an electrical signal and outputting it.

Figure 6:
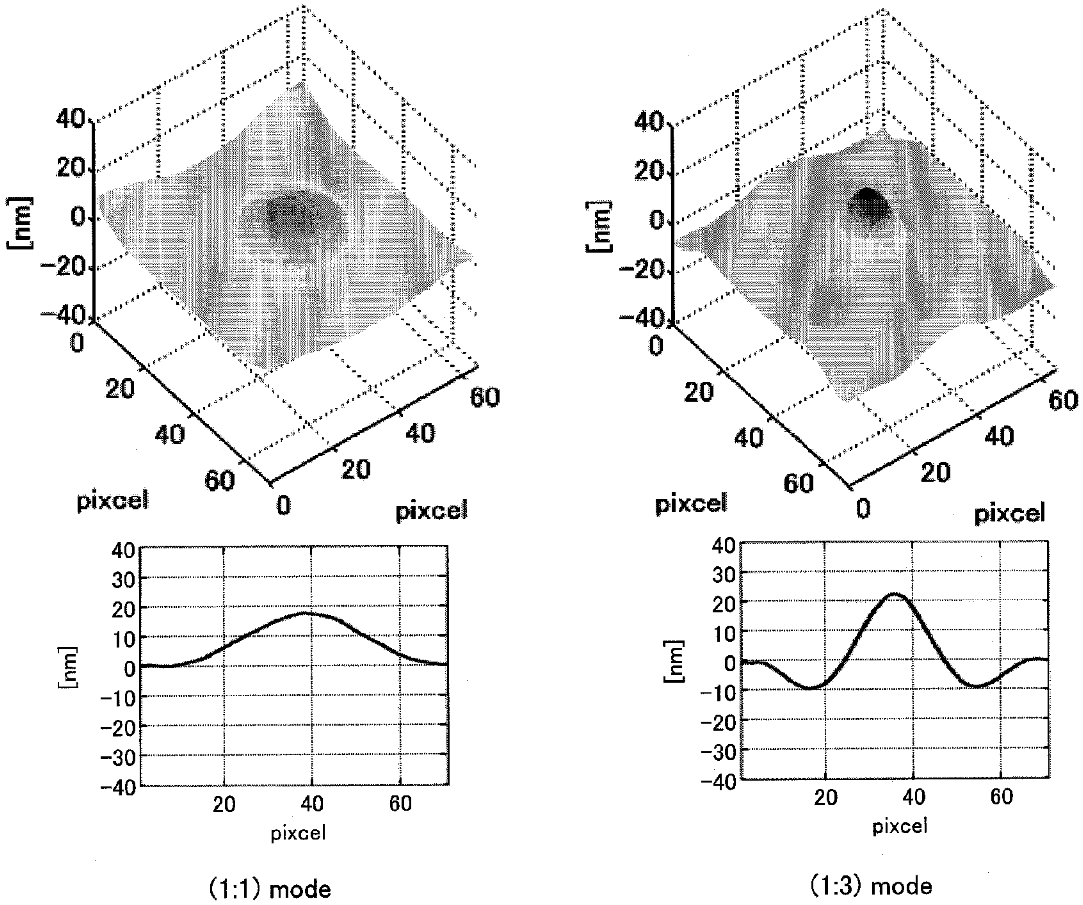
FIG. 6 shows charts indicating vibration modes of a regular hexagonal cell CMUT.
Figure 7:
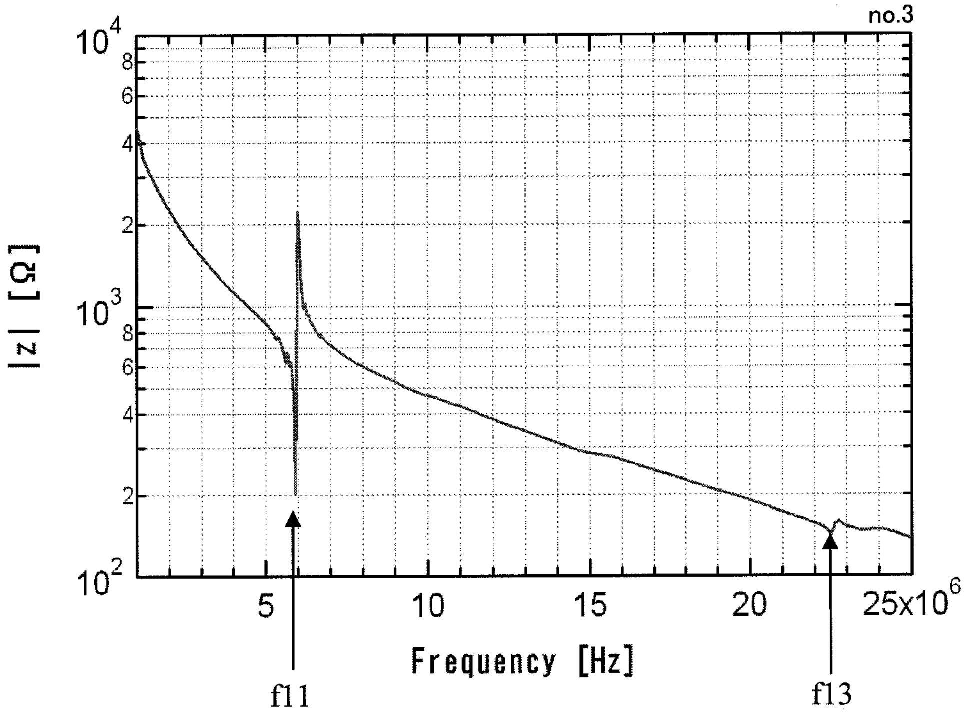
FIG. 7 is a chart indicating the impedance of a regular hexagonal cell CMUT.

Next, vibration modes of a diaphragm of a CMUT are described. A diaphragm of a CMUT may be excited in various vibration modes. Examples of the vibration modes of a regular hexagonal cell are shown in FIG. 6. The chart on the left shows the mode shape of a vibration mode referred to as a fundamental mode. The fundamental mode is a mode in which the diaphragm as a whole vibrates in phase (this will be referred to as the (1:1) mode). Accordingly, there is one vibration anti-node. On the other hand, the chart on the right is such that, near the center of the diaphragm and near supporting walls located apart from the diaphragm center, there exist anti-nodes whose phases are in opposition by approximately 180 degrees (this will be referred to as the (1:3) mode). The impedance characteristics of the diaphragm of the regular hexagonal cell discussed above in air are shown in FIG. 7. The peak on the low frequency side in the chart is the resonance point of the fundamental mode, and the peak on the high frequency side is the resonance point of the (1:3) mode. While the absolute values of the resonance frequencies of the fundamental mode and high-order mode vary depending on cell size, the value obtained by normalizing the resonance frequency of the high-order mode with the resonance frequency of the fundamental mode does not vary. Assuming that the resonance frequency of the fundamental mode is f11, and that the resonance frequency of the (1:3) mode is f13, f13/f11 would always be a uniform value (approximately 3.8). Although a case where the cell is in the shape of a regular hexagon has been presented above, the normalized frequency of a high-order mode would generally be the same for a circular shape as well. In other words, if the distance from the center of the diaphragm to the supporting walls is uniform and not dependent on direction, the high-order mode to fundamental mode resonance frequency ratios would be close in value (Non-Patent Document 1).

Figure 8:
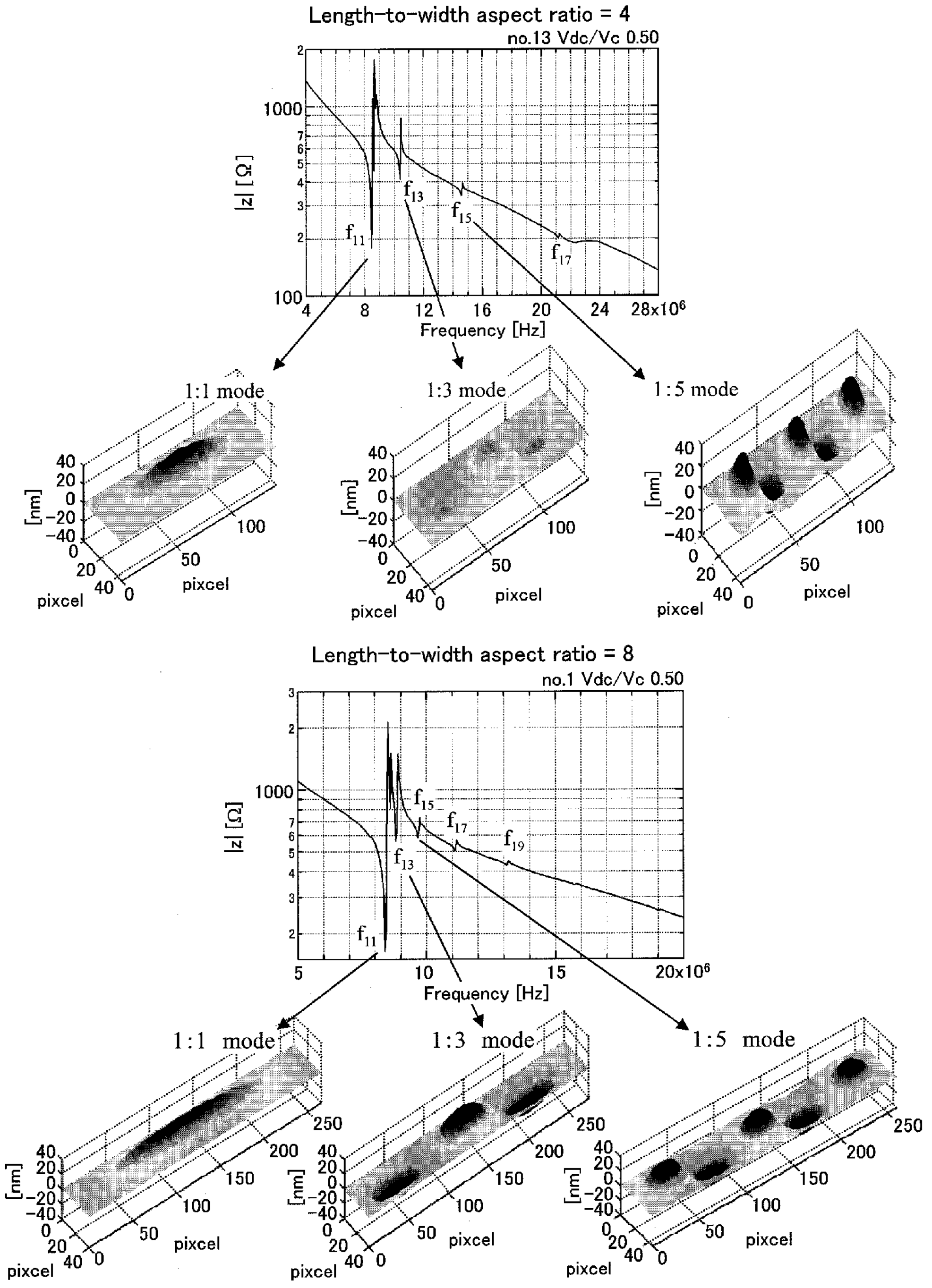
FIG. 8 shows charts indicating vibration modes and the impedance of a rectangular cell CMUT.
Figure 9:
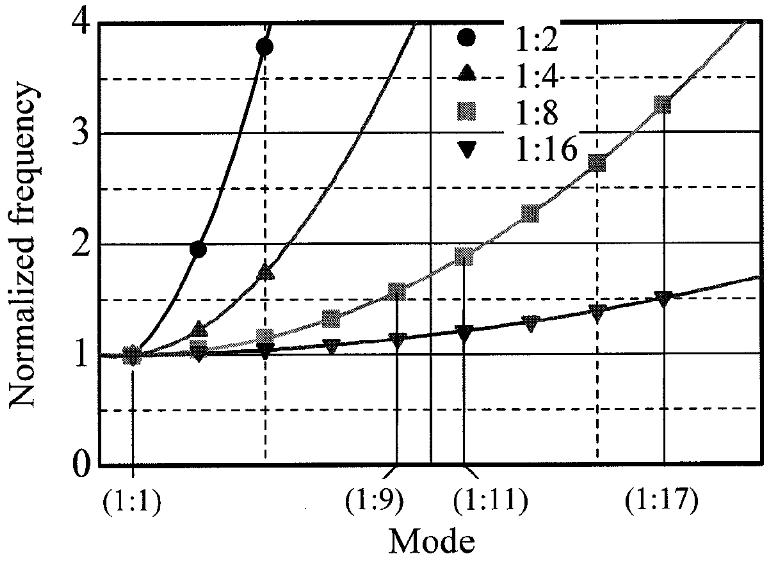
FIG. 9 is a chart indicating vibration mode frequencies of a rectangular cell CMUT.

On the other hand, in the case of an elongate rectangular cell such as that shown in FIG. 2, the excited vibration mode characteristics vary significantly from those of cases where the cell shape is regular hexagonal or circular. In cases where the cell shape is rectangular, there exist, besides the overall size, parameters in the direction of the long side and in the direction of the short side (the long side will herein be referred to as the length, and the short side as the width). Examples of the vibration modes for cases where the length-to-width aspect ratios (l/w in FIG. 2) are "4" and "8" are shown in FIG. 8. As can be seen in FIG. 8, while resonance frequency f11 of the fundamental mode remains the same even when the length-to-width aspect ratio is varied, the high-order mode frequencies vary. In the case of a rectangular cell, the frequency of the fundamental mode is determined by width w, however because the high-order modes occur in such a manner that a plurality of anti-nodes are created in the lengthwise direction, the frequencies are determined by the length. Thus, even if the widths are the same, if the length-to-width ratios are different, the frequencies of the high-order modes would vary, and the ratios of the high-order mode frequencies to the fundamental mode frequency would thus also vary. If the perimeter of the rectangle is clamped, the vibration modes that may be excited would theoretically be expressed by the equation below.

$$f_{res} \propto \frac{\pi}{2}\left[\frac{G_1^4}{w^4} + \frac{G_2^4}{l^4} + \frac{2J_1J_2}{w^2l^2}\right]^{1/2} \quad \text{[Eq. 1]}$$

where w and l are the width and length of the rectangle, and G and J are constants determined by boundary conditions. The vibration modes of rectangles have a characteristic where, as the length-to-width aspect ratio increases, the high-order modes converge towards the frequency of the fundamental mode. Results obtained by normalizing the high-order mode frequencies by the fundamental mode frequency while varying the length-to-width ratio of a rectangle are shown in FIG. 9. As can be seen in FIG. 9, as the length-to-width aspect ratio increases, the high-order frequencies converge towards the fundamental mode frequency (approaching 1), and the gradients of the curves in the chart consequently decrease. In the case of a hypothetical and infinitely large length-to-width ratio, all modes would converge at one frequency (all modes would be such that normalized frequency=1). It is noted that although, for display purposes, only 1:2, 1:4, 1:8, and 1:16 are shown in FIG. 9, curves for other length-to-width aspect ratios exist along a continuum among the curves shown in FIG. 9. By way of example, there exist curves corresponding to length-to-width aspect ratios of 1:3, 1:5, 1:6, 1:7, 1:9, 1:10, 1:11, 1:12, 1:13, 1:14, 1:15, 1:17, 1:18 . . . Further, the length-to-width aspect ratio is not restricted to integer ratios such as those discussed above, and may also include cases where it is expressed in decimal numerical values, as in 1:16.1, 1:16.5, for example.

Figure 10:
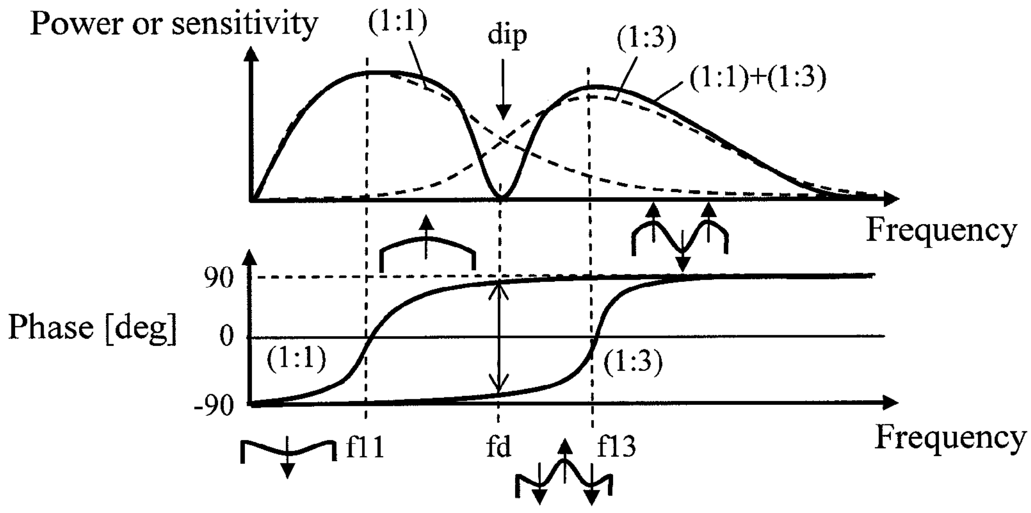
FIG. 10 shows charts indicating a dip forming mechanism for a case where a plurality of vibration modes exist.

Next, problems resulting from such vibration modes are described. The acoustic frequency characteristics of a CMUT are shown in FIG. 10 where the resonance frequency of the fundamental mode is f11 and the resonance frequency of a high-order mode with two anti-nodes is f13. In this case, a state is assumed where there is contact with a medium such as water, an acoustic lens, etc., as a load. The upper chart indicates transmit acoustic pressure or sensitivity, and the lower chart indicates the phase of each vibration mode. The term phase as used above refers to the phase difference of the acoustic pressure (or the speed or displacement of the diaphragm) with respect to the AC voltage applied across the electrodes of the CMUT. The points at which the phase is 0 are resonance points, and the phase differs by 180 degrees at the limits on the low frequency side and high frequency side of the resonance points. The phase of the high-order mode varies depending on the position along the diaphragm. However, in this case, since the focus is on the acoustic pressure that is ultimately radiated, the net phase is defined. By way of example, in the case of the (1:3) mode with respect to a rectangular diaphragm, anti-nodes with phases that differ by 180 degrees are created at the center of the diaphragm and on both sides thereof in the lengthwise direction. While the anti-node at the center is singular, two anti-nodes are created around it. Thus, with respect to the net amplitude, the direction in which two anti-nodes are created bears significance. Accordingly, the phase of the (1:3) mode is defined as the direction in which there are two anti-nodes. Since the diaphragm as a whole vibrates in phase in the fundamental mode, in general, as compared to high-order modes, the net amplitude is greater and sensitivity higher. As can be seen in FIG. 10, there exists frequency fd between f11 and f13 where the amplitude drops (sensitivity drops) locally (hereinafter referred to as a dip). The reason such a dip occurs is because the fundamental mode and the high-order mode cancel each other out. Specifically, it is because there exists a frequency at which the difference between the phase of the fundamental mode and the phase of the high-order mode becomes greater (close to 180 degrees). When the phase difference is 0 degrees, the amplitude increases because they reinforce each other. However, as the phase difference becomes closer to being mutually inverted (180 degrees), a state is created where their amplitudes cancel each other out. However, even if the phase difference is sufficiently large, if the amplitudes are small, their influence is minimal (e.g., the amplitude of f13 near f11 is small, and although the phase difference is large, the canceling amplitude is small). Thus, dips are formed locally based on a combination of phase difference and amplitude.

In general, high sensitivity and wideband characteristics are desired for ultrasonic transducers. Accordingly, it is preferable that the band around the fundamental mode be wide. However, it is undesirable for bandwidth to be narrowed by the occurrence of dips due to the existence of high-order modes. In addition, for an ultrasonic probe that utilizes sound waves of various frequencies, it would be inappropriate for the transmit acoustic pressure to drop locally only around the frequency of a dip. As already discussed above, in the case of circular or regular hexagonal cell shapes, since the frequency of a high-order mode is fixed at a constant ratio with respect to the frequency of the fundamental mode, the dip position is uniquely determined.

Accordingly, band improvement is, in principle, difficult. On the other hand, in the case of elongate cell shapes such as rectangles, the frequency of each high-order vibration mode is determined by the length-to-width aspect ratio. Thus, the dip position may be controlled by varying the length-to-width aspect ratio. However, a high-order mode of a rectangle occurs at a position that is closer to the fundamental mode frequency than is a high-order mode of a circle or a regular hexagon. Specifically, a dip of a rectangle would actually be in a direction that narrows the band of the fundamental mode, and would be in the opposite direction to improving wide band characteristics.

Figure 11:
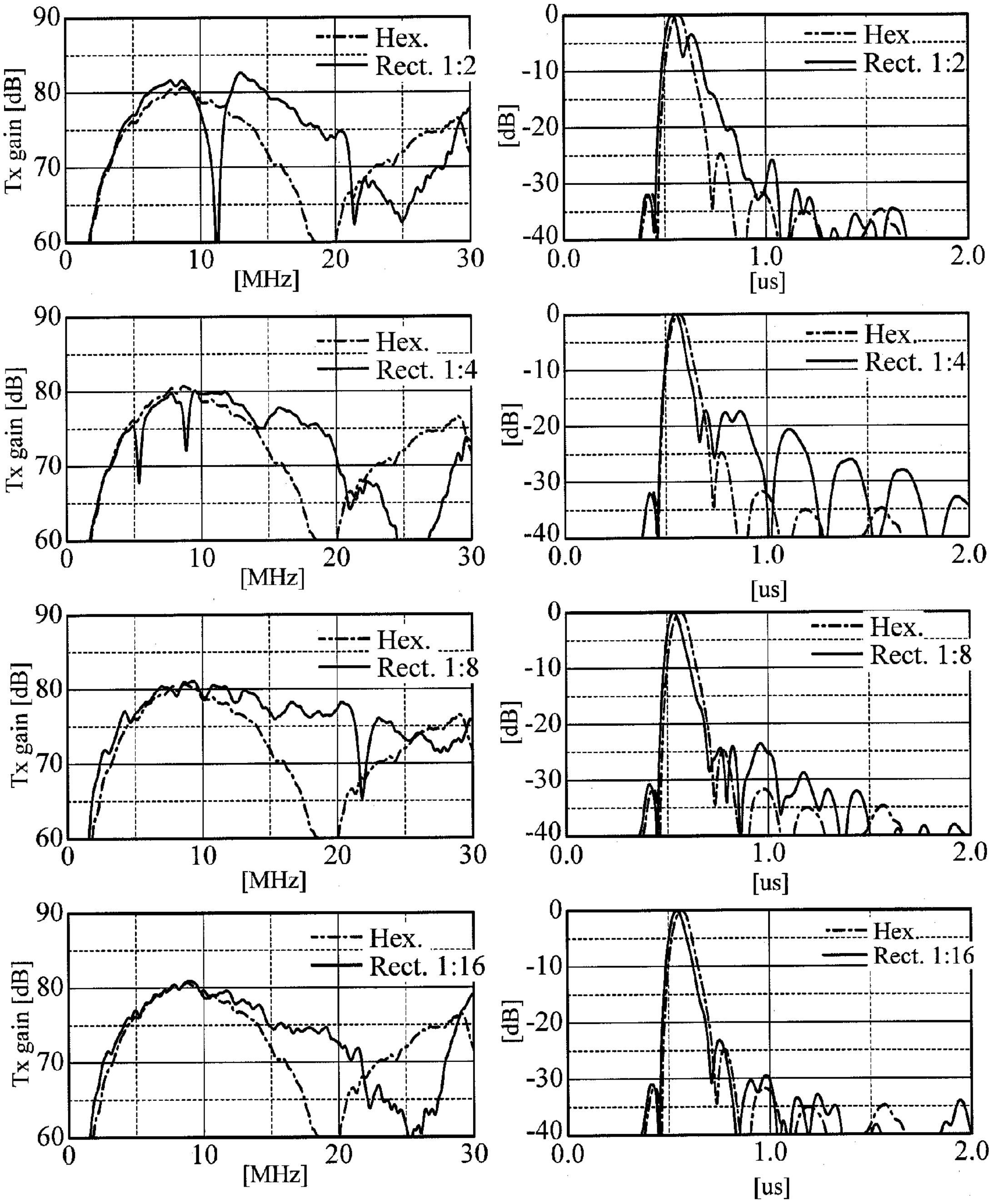
FIG. 11 shows charts indicating transmission gains and pulse responses of a rectangular cell CMUT and a hexagonal cell CMUT.

By way of example, experiment results for transmit sensitivity with respect to CMUT cells whose length-to-width aspect ratios were “2,” “4,” “8,” and “16” are shown in FIG. 11. By way of comparison, results for a regular hexagonal cell (HEX) are also shown. In the case of the regular hexagonal cell, the band center of the fundamental mode is approximately 9 MHz, and a significant dip occurs near 20 MHz. On the other hand, in the case of the rectangular cells, the band of the fundamental mode is wider than that of the regular hexagonal cell and is equal to or wider than 25 MHz. However, at small length-to-width aspect ratios, sharp dips are observed within the fundamental mode band. By way of example, when the length-to-width aspect ratio is “2,” there is a sharp dip at around 11 MHz, and when the length-to-width aspect ratio is “4,” there are sharp dips at around 5 MHz and 8 MHz. In general, in the case of transmission and reception, the frequency band of an ultrasonic probe is defined by the frequency width within which there is a −6 dB difference relative to the peak value. In the case of transmission only or reception only, it is defined by half the value thereof, namely −3 dB. However, in the cases in FIG. 11 where the length-to-width aspect ratios are “2” and “4,” since their dips are equal to or deeper than 10 [dB], their bandwidths would be considerably narrower than that of a hexagonal cell.

Figure 12:
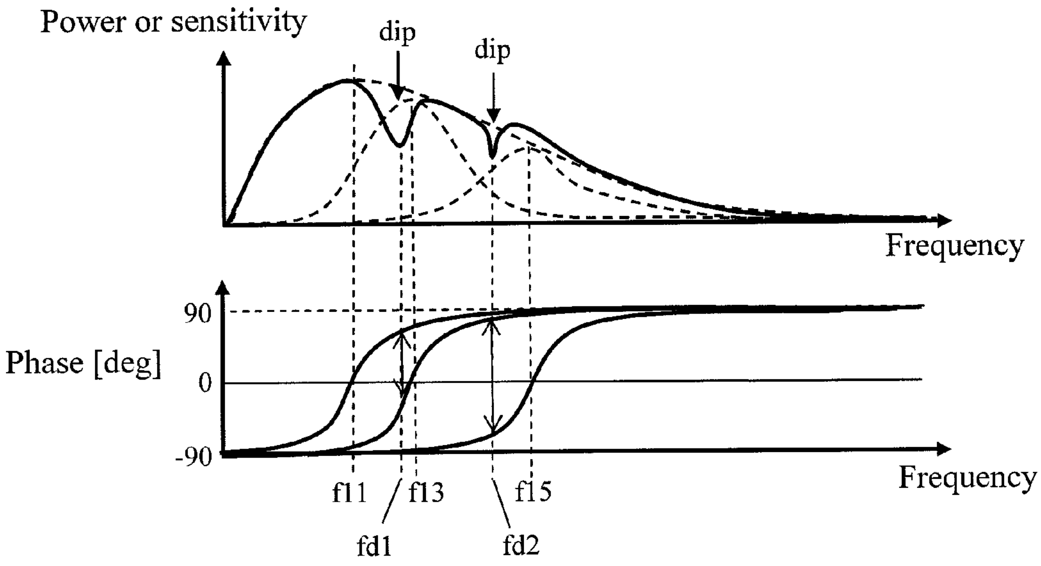
FIG. 12 shows charts indicating a dip forming mechanism for a case where intervals among a plurality of vibration mode frequencies have narrowed.

On the other hand, from the present experimental data, it can be seen that the interval between the dips becomes narrower as the length-to-width aspect ratio of the rectangle increases, and also that the depths of the dips become less. By way of example, the depths of the dips when the length-to-width aspect ratio is “8” are fractions of those when the length-to-width aspect ratio is “4.” Further, it can be seen that the depths of the dips become even smaller when the length-to-width aspect ratio is “16.” The principles thereof are shown in FIG. 12. The frequency characteristics related to three vibration modes are shown in FIG. 12. Since the frequency intervals among the respective vibration modes approach the fundamental mode as the length-to-width aspect ratio increases, the intervals at which dips are created also become narrower. Further, as the resonance frequencies of the respective vibration modes become closer, the phase differences of the vibration modes also become smaller (fd1 in the figure). Further, at regions where two or more vibration modes overlap, since there exist both a mode that is close to being in phase with the fundamental mode and a mode that is close to being out of phase, extreme dip formations are suppressed (fd2 in the figure). Thus, due to interference between two or more vibration modes, the positions and depths of dips vary.

Figure 13:
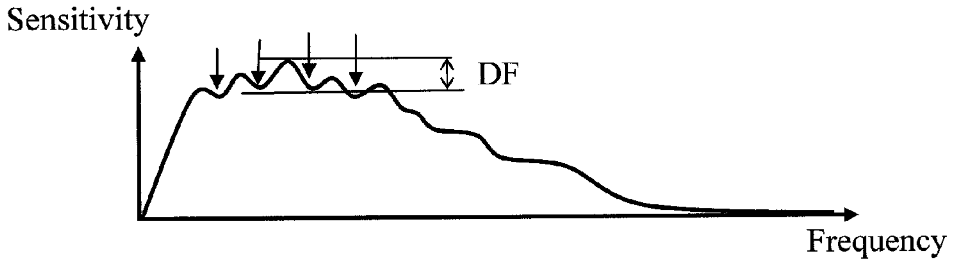
FIG. 13 is a chart indicating the frequency characteristics and dip of a CMUT.

Utilizing the above-mentioned characteristics of interference among the vibration modes of a rectangular diaphragm, the influences of dips may be reduced even for rectangles. Although the number of dips occurring within the fundamental mode band increases as the length-to-width aspect ratio increases, the depths of the dips decrease. Accordingly, dips would ultimately not occur if the length-to-width aspect ratio is infinitely large. Although an infinite length-to-width aspect ratio is not actually possible, there exists a threshold that poses no problem for actual use if the dips become sufficiently small. In the case shown in FIG. 11 where the length-to-width aspect ratio is “8,” several dips occur within the fundamental mode band, but the depths of the dips are only approximately −2 dB relative to the maximum value. Further, at a length-to-width aspect ratio of “16,” the dips are generally equal to or below 1 dB. Based on the results in FIG. 11 for the length-to-width aspect ratios of “8” and “16,” it can be seen that, if the dips are sufficiently negligible, rectangular cells are more wide band in characteristics than hexagonal cells. By having the length-to-width aspect ratio be of or above a given value (for rectangular cells, a length-to-width aspect ratio of or above “8”), spurious response may be reduced, and an ultrasonic probe that is more wide band than conventional CMUTs may be attained. In terms of actual design, the length-to-width aspect ratio may be defined as follows. FIG. 13 shows in terms of frequency characteristics the transmit/receive sensitivity of a CMUT for a given length-to-width aspect ratio. When the length-to-width aspect ratio is finite, there always occurs one or more dips in the frequency characteristics. So long as the depths of all dips are equal to or below 6 dB at most (or 3 dB in the case of transmission or reception only), it may be said that the band of the ultrasonic transducer is not dependent on dips for practical purposes. Accordingly, the length-to-width aspect ratio may be designed such that the depths of the dips caused by interference between the fundamental mode and high-order modes that occur in the lengthwise direction (DF in FIG. 13) would be equal to or less than 6 dB for transmission and reception.

[Second Embodiment]

In FIG. 11, there are shown not only frequency characteristics, but also time response envelopes of transmit sound waves. With ultrasonic imaging devices, etc., envelope width greatly affects image resolution. Accordingly, envelope width becomes an important evaluation element. When the length-to-width aspect ratio is small and the dips are large, the signal level following the main pulse is greater than it is for hexagonal cells, and so-called ringing (tailing) occurs. When such ringing occurs, it may potentially become a noise component when performing imaging with an ultrasonic diagnostic device, etc. Accordingly, in actual use, a waveform in which ringing is reduced as much as possible is required. It can be seen in FIG. 11 that at length-to-width aspect ratios of "8" and above, ringing is brought to levels generally comparable to that of a hexagonal cell (approximately −25 dB or less).

Ordinarily, the dynamic range of signals used in ultrasonic diagnostic devices is 50 to 60 dB or greater. If the purpose is to image living organisms, the standard imaging region is approximately 10 cm in depth from the body surface, and the sensitivity band of probes that are most often used with such depths is generally 10 MHz or less. The attenuation coefficient of living organisms is said to be generally the same as water, namely, approximately 0.5 [dB/cm/MHz]. By way of example, if one were to perform imaging up to a depth of 10 cm at 5 MHz, the signal transmitted from the probe would be attenuated by 0.5 [dB/cm/MHz]×10 [cm]×2×5 [MHz]=50 dB as it travels to and from a reflection point within the living organism. Accordingly, under such circumstances, a signal dynamic range (DR) of approximately 50 dB would be demanded of the probe. For this reason, ordinarily, for medical ultrasonic diagnostic devices, etc., approximately 50 dB is secured for the transmit/receive sensitivity dynamic range (DR). Accordingly, if, for transmission and reception, there is any spurious response, such as ringing, etc., at a level of at least 50 dB or greater in transmit pulse, there is a possibility that a drop in performance may be caused, such as image resolution degradation, etc. From such a perspective, it is demanded that ringing caused by interference between the fundamental mode and high-order modes be 50 dB or less for transmission and reception, and that it be half that, namely 25 dB or less, for transmission only or reception only.

Figure 14:
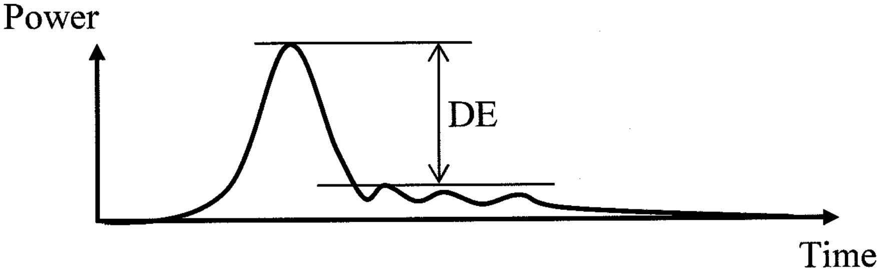
FIG. 14 is a chart indicating the relationship between the main pulse of an envelope and ringing (tailing).

In actual design, with the present invention, the length-to-width aspect ratio may be defined as follows. FIG. 14 shows a time waveform envelope of a transmit sound wave or a receive signal. The length-to-width aspect ratio should be made to be such that the difference between the maximum of this waveform and the ringing level (DE in the chart) would be 25 dB or greater, or for transmission and reception, 50 dB or greater. It would thus be possible to attain a time waveform with a narrow practical pulse width.

[Third Embodiment]

In the second embodiment, a frequency and depth that suit a specific purpose are set, but conditions may vary for other purposes. By way of example, even if the purpose is the same, that is, imaging living organisms, a shallower region may sometimes be imaged at a higher resolution using a higher frequency wave. For example, for imaging up to approximately 3 cm at 20 MHz, the minimum requisite dynamic range would be 0.5 [dB/cm/MHz]×3 [cm]×2×20 [MHz]=60 dB. According to the results in FIG. 11, the transmit gain ringing level when the length-to-width aspect ratio is "16" is approximately −30 dB. In other words, it corresponds to a DE of approximately 60 dB for transmission and reception. Accordingly, this signifies that the length-to-wise aspect ratio of the rectangle under the present conditions is "16" and above.

Figure 15:
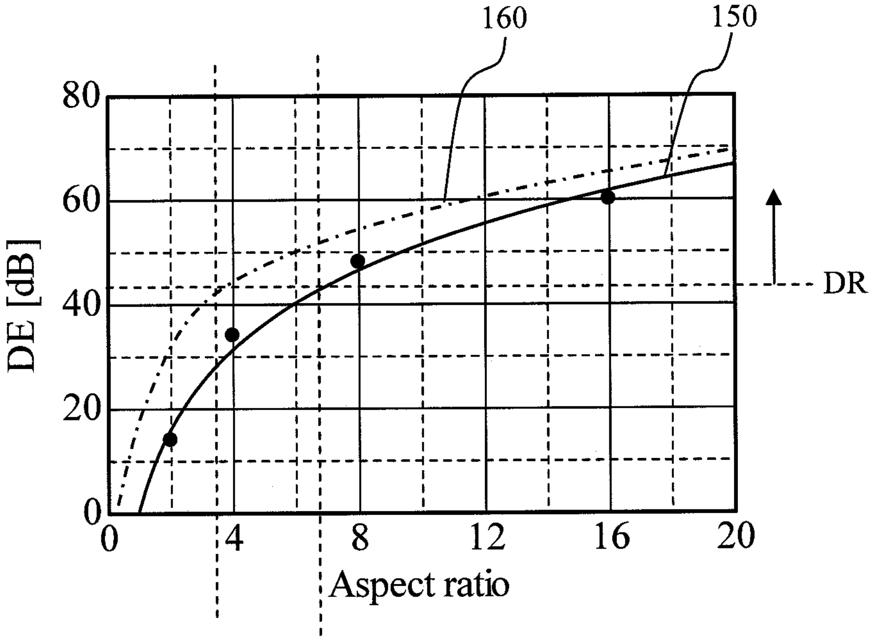
FIG. 15 is a chart indicating the length-to-width ratio dependence of the level difference (dynamic range) between the main pulse of an envelope and ringing (tailing).

To sum up the above, a method for setting the length-to-width ratio may be defined in more general terms as follows. Based on experiment data, the relationship between length-to-width aspect ratio and DE for transmission and reception is shown in FIG. 15. Each point in the chart is experiment data, and curve 150 is fitted with a logarithmic curve. Using FIG. 15, once the minimum requisite dynamic range (DR) is determined, then the requisite difference (DE) between the maximum of the transmit and receive envelope and the ringing level would automatically be determined, and the requisite length-to-width aspect ratio would consequently be determined. As mentioned above, the requisite dynamic range may be calculated through a transmit and receive attenuation formula, i.e., attenuation coefficient [dB/cm/MHz]×imaging depth [cm]×2×used frequency [MHz]. However, as would be expected, DE may not necessarily always be determined as a unique value. Specifically, in cases where resolution may be sacrificed, and so forth, the ringing level may vary. However, in that case, the standard may be reset by recalculating a curve similar to that in FIG. 15 with respect to the ringing level demanded in accordance with the purpose, and it does not change the method itself of setting the length-to-width aspect ratio, which is one point of the present invention. By way of example, with respect to FIG. 15, a peak that exists after the pulse width at the −10 dB position along the hexagonal cell envelope shown in FIG. 11 was recognized as the ringing level. However, with respect to specifications that do not demand as high a resolution as that of a hexagonal cell, the value deemed to be the ringing level drops, and DE consequently increases overall. As a result, it may sometimes resemble curve 160 in FIG. 15. In this case, even if the DR is the same, the requisite length-to-width aspect ratio would be approximately "4" or greater.

[Fourth Embodiment]

The present invention is also able to set optimal length-to-width aspect ratios based on the resonance frequency of each vibration mode. In the first and second embodiments, it was indicated that a wide band or a short pulse could be attained with respect to frequency characteristics or a time waveform by having the length-to-width aspect ratio of the rectangle be "8" or greater. On the other hand, according to the results in FIG. 8, an increase in length-to-width aspect ratio corresponds to a decrease in resonance frequency for each vibration mode with respect to the fundamental mode. In the case of a length-to-width aspect ratio of "8," the (1:11) mode, which is fifth in order counting from the (1:1) mode, is equal to or less than twice the resonance frequency of the (1:1) mode. In other words, when there are six or more vibration modes for which an odd number of anti-nodes exist in the region where the normalized frequency is 2 or less, the length-to-width aspect ratio becomes "8" or greater.

Accordingly, in an actual design for attaining wide band characteristics equivalent to or greater than a regular hexagonal cell, the length-to-width aspect ratio should be made to be such that there are six or more vibration modes for which an odd number of anti-nodes exist in the region where the normalized frequency is 2 or less.

[Fifth Embodiment]

Figure 16:
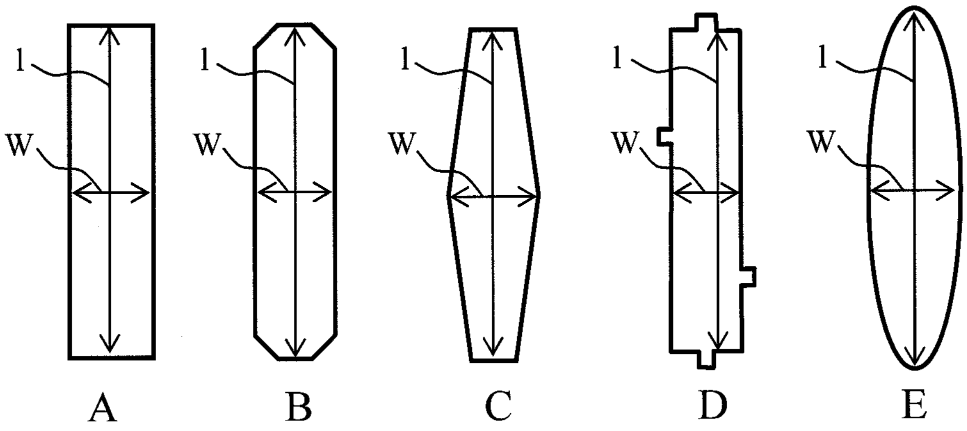
FIG. 16 is a diagram showing various rectangle-based cell shapes.

In the first to fourth embodiments, methods for setting a length-to-width aspect ratio were presented with respect to cases where the cell shape was rectangular. However, actual cell shapes are not necessarily limited to those that are strictly rectangular. As shown in FIG. 16, there are innumerable cell shapes where the distance from the center of the diaphragm to the supporting walls is not uniform. It is noted that A shows an example of a rectangle, B an octagon, C a hexagon, D a rectangle with fine bumps/dents, and E an ellipse. The shape may of course be some other shape than those in FIG. 16. However, as can be seen in the diagram, by defining the representative aspect ratio (=l/w) as being between the lengths in the direction in which the gap between the supporting walls is narrow (W) and in the direction in which it is long (l), the optimal aspect ratio may be set through the methods discussed in the first to fourth embodiments. It is noted that, in cases where there are fine bumps/dents, it is assumed that the lengths in the direction in which the gap between the supporting walls is narrow (W) and in the direction in which it is long (l) are given by the sides disregarding the fine bumps/dents, or by the lengths between apices, or by average lengths. In addition, the example in D shows an example where the fine bumps/dents are so formed as to expand the perimeter of the rectangle, which is the original figure. However, they may also be formed so as to narrow the perimeter of each side inward relative to the original figure. In addition, it is assumed that the widths and depths of the fine bumps/dents are sufficiently small relative to the lengths in the direction in which the gap between the supporting walls is narrow (W) and in the direction in which it is long (l). The expression "sufficiently small" as used above refers to an extent that does not compromise the original figure, or an extent that does not significantly alter the time response envelopes shown in FIG. 11, for example, from the characteristics of the original figure.

| List of Reference Numerals | |
|---|---|
| 1: | Substrate |
| 2: | Lower electrode |
| 3: | Upper electrode |
| 4: | Insulator |
| 5: | Diaphragm |
| 6: | Acoustic medium |
| 7: | Cavity |
| 8: | Supporting wall |
| 9: | Backing material |
| 10: | Capacitive micro-machined ultrasonic transducer |
| 30: | Connector part |
| 31: | Lead wire |
| 32: | Upper electrode connection pad |
| 33: | Lower electrode connection pad |
| 40: | Transmission and reception switch |
| 41: | Voltage limiter |
| 42: | Power supply |
| 43: | Transmission amplifier |
| 44: | Reception amplifier |
| 45: | Direct power supply |
| 46: | D/A converter |
| 47: | A/D converter |
| 48: | Transmission beam former |
| 49: | Reception beam former |
| 50: | Controller unit |
| 51: | Signal processor |
| 52: | Scan converter |
| 53: | Display |
| 54: | User interface |
| 150: | Curve indicating aspect ratio dependence (relative to the time at which a transmit envelope of a regular hexagonal cell is −10 dB) with respect to the difference between a transmit and receive waveform envelope peak and ringing level |

-continued

| List of Reference Numerals | |
|---|---|
| 160: | Curve indicating aspect ratio dependence (relative to a time equal to or greater than the time at which a transmit envelope of a regular hexagonal cell is −10 dB) with respect to the difference between a transmit and receive waveform envelope peak and ringing level |
| 210: | Acoustic lens |
| 220: | Acoustic matching layer |
| 240: | Conductive film |
| 300: | CMUT array |
| 2000: | Ultrasonic probe |
| A: | Rectangle |
| B: | Octagon |
| C: | Hexagon |
| D: | Rectangle with fine bumps/dents |
| E: | Ellipse |

The invention claimed is:

1. An ultrasonic probe comprising:

a capacitive micro-machine, wherein the capacitive micro-machine comprises:

a substrate having a first electrode; and a diaphragm having a second electrode, wherein the diaphragm has its peripheral parts secured to the substrate by means of supporting walls rising from the substrate, wherein a cavity is formed between the substrate and the diaphragm, and is of a cell shape where a distance from the center of the diaphragm to the peripheral parts at which the diaphragm is secured is not uniform, wherein a ratio between a length of the diaphragm in the direction of a first axis and a length in the direction of a second axis perpendicular to the first axis is taken to be a representative aspect ratio, and wherein the representative aspect ratio is set to a value at which a signal level of a locally occurring frequency at which amplitude drops or sensitivity drops within a bandwidth of at least one of transmission and reception by the ultrasonic probe can be suppressed below a predetermined value, and wherein the representative aspect ratio is set a value at which, among vibration modes of the diaphragm, there are six or more vibration modes for which a value obtained by dividing a frequency of a vibration mode having an odd number of anti-nodes by a fundamental mode frequency is 2 or less.

2. The ultrasonic probe according to claim 1, wherein the representative aspect ratio is set to a value at which a dip of 6 dB or greater is not formed within a transmit or receive band of the ultrasonic probe.

3. The ultrasonic probe according to claim 1, wherein the representative aspect ratio is set to a value at which a dip of 3 dB or greater is not formed within a transmit or receive band of the ultrasonic probe.

4. The ultrasonic probe according to claim 1, wherein the representative aspect ratio is "8" or greater.

5. The ultrasonic probe according to claim 1, wherein the representative aspect ratio is so set that a ringing level of a transmit sound wave or receive signal is 50 dB or less.

6. The ultrasonic probe according to claim 1, wherein the representative aspect ratio is so set that a ringing level of a transmit sound wave or receive signal is 25 dB or less.

7. The ultrasonic probe according to claim 1, further comprising an ultrasonic probe array in which a plurality of the capacitive micro-machines are arranged.

8. The ultrasonic probe according to of claim 1, wherein the representative aspect ratio is so set as to be equal to or greater than a ratio calculated based on a minimum requisite dynamic range (DR) and on a difference (DE) between a transmit and receive envelope maximum and ringing level.

9. An ultrasonic imaging device comprising:

an ultrasonic probe;

a direct power supply part and an alternating power supply part;

a transmission beam former that is a means that transmits an ultrasonic beam from the ultrasonic probe;

a reception beam former that forms a reception beam from an ultrasonic signal received at the ultrasonic probe;

a signal processor that processes a signal from the reception beam former; and display means that displays image data corresponding to a processing result of the signal processor, wherein the ultrasonic probe comprises a capacitive micro-machine, the capacitive micro-machine comprises: a substrate having a first electrode; and a diaphragm having a second electrode, wherein the diaphragm has its peripheral parts secured to the substrate by means of supporting walls cavity is formed between the substrate, wherein a cavity is formed between the substrate and the diaphragm and is of a cell shape where a distance from the center of the diaphragm to the perpheral parts at which the diaphragm is secured is not uniform, wherein a ratio between a length of the diaphragm in the direction of a first axis and a length in the direction of a axis perpendicular to the first axis is taken to be representative aspect ratio, wherein the representative aspect ratio is set to a value at which a signal level of a locally occurring frequency at which amplitude drops or sensitivity drops within a bandwidth of at least one of transmission and reception by the ultrasonic probe can be suppressed below a predetermined value, and wherein the representative aspect ratio is to a value at which, among vibration modes of the diaphragm, there are six or more vibration modes for which a value obtained by dividing a frequency of a vibration mode having an odd number of anti-nodes by a fundamental mode frequency is 2 or less.

10. The ultrasonic imaging device according to claim 9, wherein the representative aspect ratio is set to a value at which a dip of 6dB or greater is not formed within a transmit or receive band of the ultrasonic probe.

11. The ultrasonic imaging device according to claim 9, wherein the representative aspect ratio is set to a value at which a dip of 3dB or greater is not formed within a transmit or receive band of the ultrasonic probe.

* * * * *